(12) United States Patent
Gau

(10) Patent No.: US 7,037,340 B2
(45) Date of Patent: May 2, 2006

(54) INTERVERTEBRAL NUCLEUS PROSTHESIS AND SURGICAL PROCEDURE FOR IMPLANTING THE SAME

(75) Inventor: Michel Gau, Ouveillan (FR)

(73) Assignee: LDR Medical, Rosieres Pres Troyes (FR)

( * ) Notice: Subject to any disclaimer, the term of this patent is extended or adjusted under 35 U.S.C. 154(b) by 0 days.

(21) Appl. No.: 10/060,862

(22) Filed: Jan. 30, 2002

(65) Prior Publication Data

US 2002/0156528 A1 Oct. 24, 2002

Related U.S. Application Data

(63) Continuation of application No. PCT/EP00/07494, filed on Aug. 2, 2000.

(30) Foreign Application Priority Data

Aug. 3, 1999 (FR) .................................. 99 10167

(51) Int. Cl.
*A61F 2/44* (2006.01)
(52) U.S. Cl. ................. 623/17.16; 623/17.14
(58) Field of Classification Search .. 623/17.11–17.16, 623/18.11
See application file for complete search history.

(56) References Cited

U.S. PATENT DOCUMENTS

| 4,865,606 | A |   | 9/1989 | Rehder |
|-----------|---|---|--------|--------|
| 5,320,644 | A | * | 6/1994 | Baumgartner ................ 623/17 |
| 5,556,431 | A | * | 9/1996 | Buttner-Janz ............ 623/17.15 |
| 5,702,454 | A |   | 12/1997 | Baumgartner |
| 5,755,797 | A |   | 5/1998 | Baumgartner |

FOREIGN PATENT DOCUMENTS

| DE | 37 26 969 | 3/1989 |
| DE | 93 04 368 | 6/1993 |
| DE | 195 27 975 | 4/1997 |
| EP | 0 577 179 | 6/1994 |
| EP | 0 621 020 | 10/1994 |

* cited by examiner

*Primary Examiner*—Bruce Snow
*Assistant Examiner*—Cheryl Miller

(57) ABSTRACT

An intervertebral nucleus prosthesis characterized in that it consists of at least one, in particular, spherical body movable in two directions of a plane and made of a rigid, non-oxidizing, biocompatible material with a diameter adapted to the biological nucleus, the spherical body being mounted non-displaceably but freely rotatably about its center in a cage and protruding at both opposite sides of said cage in the form of a spherical caps. Also proposed is a method for implanting such a prosthesis.

15 Claims, 2 Drawing Sheets

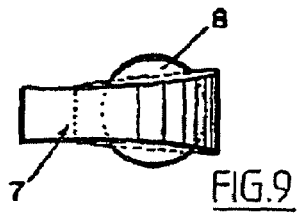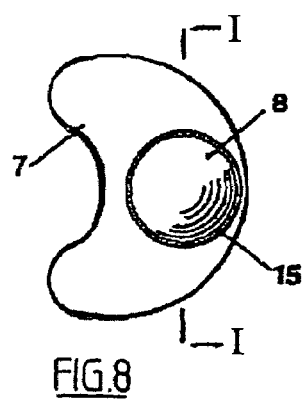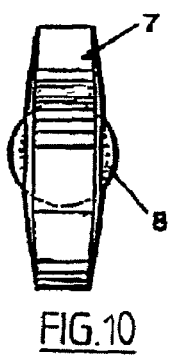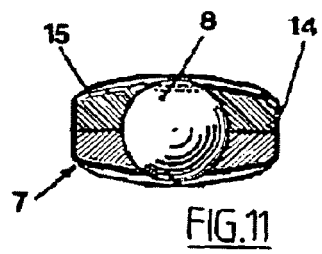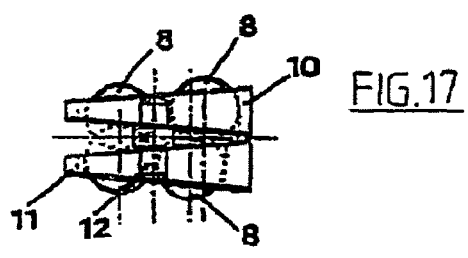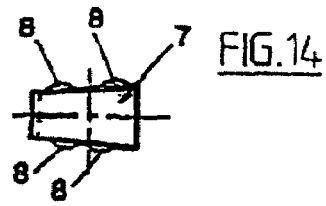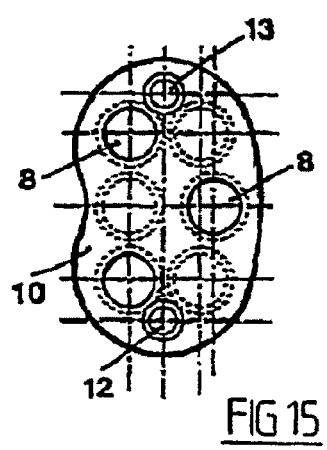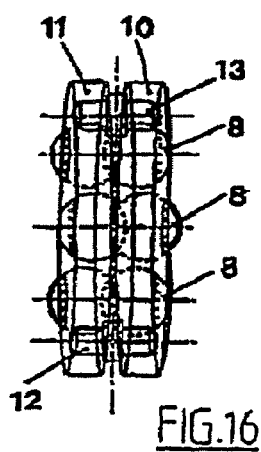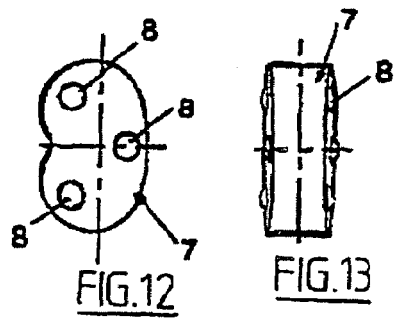

INTERVERTEBRAL NUCLEUS PROSTHESIS AND SURGICAL PROCEDURE FOR IMPLANTING THE SAME

CROSS REFERENCE TO RELATED APPLICATIONS (NOT APPLICABLE)

This application is a continuation of international application number PCT/EP00/07494 filed on Aug. 2, 2000.

STATEMENT REGARDING FEDERALLY SPONSORED RESEARCH OR DEVELOPMENT (Not applicable)

INCORPORATION BY REFERENCE OF MATERIAL SUBMITTED ON A COMPACT DISC (Not applicable)

BACKGROUND OF THE INVENTION

1. Field of the Invention

The invention relates to an intervertebral nucleus prosthesis for restoring mobility in the area of an intervertebral disc. This mobility is created physiologically by the nucleus, which can be seen as a mechanical joint component of the vertebral bodies.

2. Description of Related Art

Physiologically, the nucleus is formed by an essentially spherical, nonextendible, but deformable body inserted like a ball between two end faces of vertebrae, essentially at the center thereof, and allowing inclining, rotating and sliding movements.

The end faces of the vertebrae themselves are surrounded by concentric layers of fibers referred to as annulus and containing fibers which cross one another obliquely from one layer to the other.

In this arrangement, the nucleus, which is actually a deformable, but nonextendible capsule filled with a hydrophilic, jelly-like substance (mucopolysaccharide), itself moves backwards or forwards during forward or backward bending movement of the spinal column, and this movement of the nucleus is limited by the back and front fibers of the annulus and by different ligaments.

When the spinal column inclines to the side, the displacement of the nucleus stretches the fibers on the convex side. The displacement is limited by the intervertebral ligaments.

During a rotation of the spinal column, the intervertebral disc is acted upon by shearing forces.

The nucleus, which is a hydrophilic body, has a specific osmotic pressure in the state of rest. Under load, the nucleus loses water. The thickness of the intervertebral disc decreases. Rehydration occurs once the pressure is reduced again.

The pathological states which affect the reciprocal movements of the various vertebral bodies are essentially overloading or excessive and repeated strain or natural aging processes.

In the event of excessive, repeated or prolonged strain, rehydration does not take place, and, consequently, the pressure exerted by the nucleus on the fibers forming the various concentric layers of the annulus is unable to be built up, and this pressure, therefore, also no longer carries out its restoring function during the movements. This results in instability accompanied by arthrosis.

The object of the invention is to prevent this instability from developing by inserting a nucleus prosthesis, implantation of which can be carried out in vivo and with less traumatization than has so far been possible with known prostheses of this kind.

These known prostheses, the principles of which will be examined hereinbelow, harbor drawbacks which, with a knowledge of the reciprocal movements and the function of the nucleus during these movements, are understandable.

These drawbacks occur during both use and insertion of these known implants.

Initially, it was simply suggested that those intervertebral discs located in the traumatized area be removed. A bony graft was then inserted, partly with and partly without osteosynthesis.

The blocking of two adjacent vertebral bodies thereby obtained did, however, merely transfer the load onto the intervertebral discs of the immediately adjacent vertebral bodies, which were thereby placed under excessive strain and quickly suffered damage. The problem was only shifted without solving it.

A complete intervertebral disc prosthesis including both annulus and nucleus has also been suggested.

The main disadvantage of this practice is that it requires total removal of the damaged intervertebral disc and then insertion of the complete prosthesis between two adjacent vertebral bodies.

Each of the two phases of this operation requires severing of the common vertebral body ligaments, namely the front ligament (LVCA) and the back ligament (LVCP), which does not allow the natural movements of the spinal column to be restored again, and this, therefore, suffers a loss of reliability.

BRIEF SUMMARY OF THE INVENTION

To avoid these disadvantages, the present invention is based on inserting a nucleus prosthesis without resecting the entire intervertebral disc. In this way, development of the instability, which causes the deterioration, can be limited by replacing the nucleus. Without damaging the annulus or the ligaments (LVCA) and (LVCP), the nucleus prosthesis allows, by displacement of the substitute nucleus, pressure to be exerted on the annulus, and the annulus to thereby be placed under tension during movement of the spinal column so that it restores the balanced position.

The center of rotation, thus restored, does, in fact, remain movable and capable of adapting to the various movements of bending forwards and backwards, stretching and inclining sideways.

The nucleus prosthesis of the present invention consists of one or several balls which are hard, smooth and non-oxidizing and which are arranged so as to be freely movable inside a rigid cage which itself is non-oxidizing. This prosthesis is able to be accommodated in the volume made available by removal of the nucleus between two end faces of vertebrae.

BRIEF DESCRIPTION OF THE SEVERAL VIEWS OF THE DRAWINGS

FIGS. 8, 9 and 10 are schematic views from the side, from above and from the front of a nucleus prosthesis with only one ball.

FIG. 11 is a schematic longitudinal sectional view, by way of example, along line I—I in FIG. 8.

FIGS. 12, 13 and 14 are schematic views from above, from the front and from the side of a nucleus prosthesis with several balls.

FIGS. 15, 16 and 17 are schematic views from above, from the front and from the side of a nucleus prosthesis with a buffer device.

DETAILED DESCRIPTION OF THE INVENTION

Figure 1:
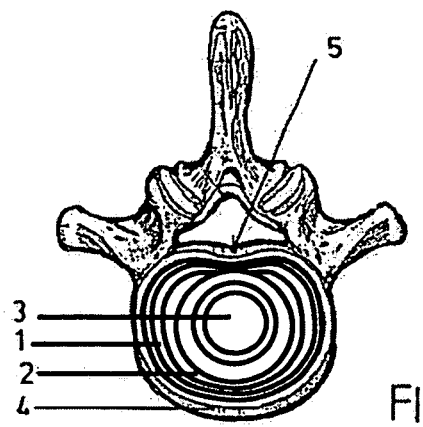
FIG. 1 is a plan view of a vertebral body showing each of the positions of the nucleus, the annulus and the front and back ligaments.
Figure 2:
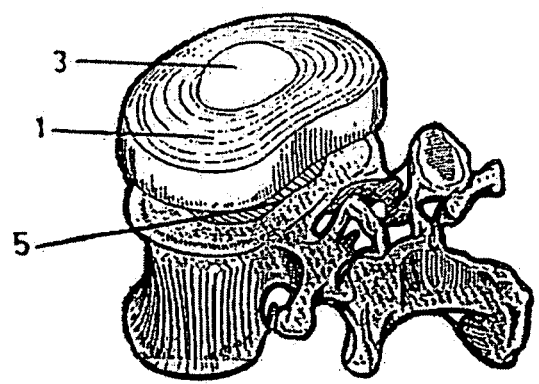
FIG. 2 is a perspective view of a vertebral body showing the annulus and the nucleus surrounded by the annulus and supported on the vertebral body.
Figure 3:
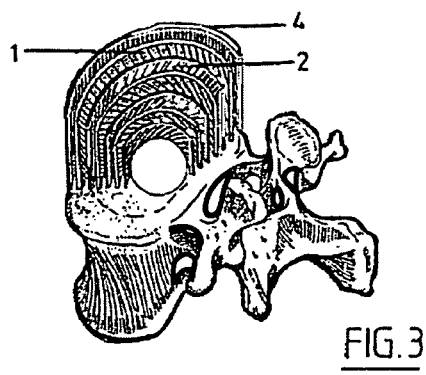
FIG. 3 is a perspective schematic view of a diametrically cut annulus showing the concentric layers of fibers crossing one another.

FIGS. 1 and 2 show clearly an intervertebral plane formed by a large number of concentric layers of intersecting fibers 1 and 2, clearly apparent from FIG. 3, at the center of which the nucleus 3 is located, while the front ligament (LVCA) 4 and the back ligament (LVCP) 5 are located at the outside.

Figure 4:
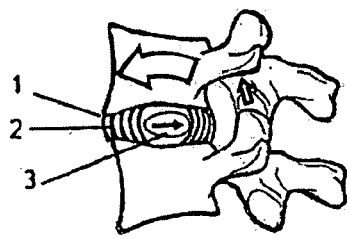
FIGS. 4 and 5 are schematic side views of two adjacent vertebral bodies during a forward and backward bending movement.
Figure 5:
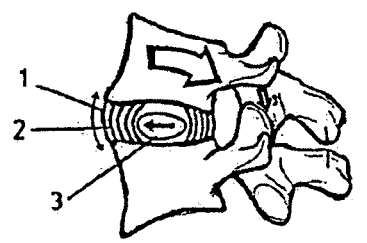

FIGS. 4 and 5 show the compression forces exerted by the nucleus 3 on the concentric layers of the annulus at the outside of the bending angle during forward or backward bending.

Figure 6:
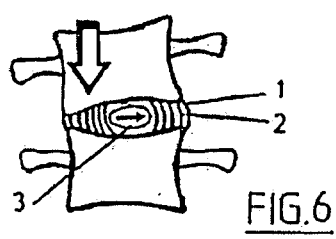
FIG. 6 is a schematic front view of two adjacent vertebral bodies during bending of the spinal column sideways.

The nucleus 3 exerts in the same way a pressure on the rings of the annulus, at the outside of the lateral angle of inclination (FIG. 6).

Each of these displacements of the nucleus 3 ensures a return to the balanced position.

Figure 7:
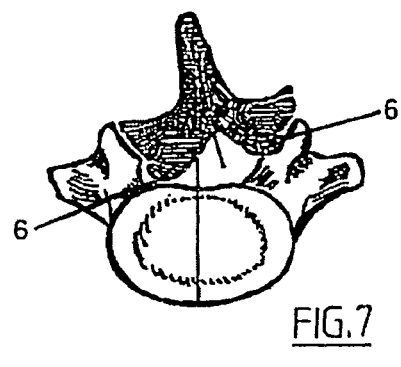
FIG. 7 is a plan view of a vertebral body during a rotatory movement.

During rotation in a horizontal plane it is the joint capsules 6 lying along an imaginary circle at the outside that enable the circular displacement and limit the rotatory movement (FIG. 7), the nucleus 3 then being acted upon by shearing forces.

In all these cases, the nucleus acts as a movement buffer and during this movement ensures return to the balanced position. The consequences of the change in the nucleus are apparent from this.

It is also apparent from this that restoration of the reciprocal movements of adjacent vertebral bodies can be achieved merely by inserting a nucleus prosthesis, implantation of which offers a very great surgical advantage.

With existing operational techniques, the surgical fusion of the vertebral bodies results in a permanent fusion of adjacent vertebrae located on either side of the damaged intervertebral disc. To this end, the intervertebral disc is completely removed.

If the fusion of two vertebral bodies by arthrodesis is successful, the problems of degeneration are then transferred to the adjacent intervertebral discs (above or below), and these problems are further increased by the rigidity of the vertebral block thus created.

If, however, the fusion is unsuccessful, which is the reason for frequent failures and results in persistence of the complaints, it is often very difficult to re-operate.

In the case of implantation of a complete prosthesis of the intervertebral disc it has been found that this necessitates a complicated and difficult surgical procedure, with a large opening being required to allow removal of the natural intervertebral disc and insertion of the complete prosthesis.

This includes the necessity of severing and displacing large abdominal vessels (aorta and venae) and the bundle of nerves of the sexual organs.

This involves the risk of extensive vascular bleeding, which is very difficult to control.

This may also lead to serious sexual problems: impotence and retrograde ejaculation.

In addition, the total resection of the intervertebral disc results in destruction of the entire annulus and the front and back intervertebral ligaments 4 and 5 and thereby creates serious instability risks.

Moreover, in this case, there is no way back, there only remains the possibility of fusion of vertebrae with the disadvantages described hereinabove.

The nucleus prosthesis according to the invention does not have any of these disadvantages. It allows replacement of the damaged nucleus in both its shape and function. It is suitable for terminating the degeneration of the intervertebral disc by restabilizing it.

The surgical implantation procedure is extremely simple. Firstly, the implantation can be carried out endoscopically. It is quick and nonaggressive.

In the event of failure, removal of the nucleus prosthesis allows recovery of the original state.

It does not involve any vascular risks or any risks for the sexual organs.

It does, in fact, suffice to endoscopically make an opening between two vertebral bodies, through the annulus, the opening being just large enough to reach and remove the damaged nucleus, and to insert in the same way the artificial nucleus, which will automatically center itself in the original cavity, and to then close the opening thus made by a suture.

Aside from the rapidity of this operation, the fibrous body which has undergone only slight damage from the incision, is able to recover spontaneously and quickly and virtually without any pain. The front and back ligaments do not undergo any traumatism, which allows the original mobility of the spinal column to be restored.

Owing to the simplicity of the implantation of this nucleus prosthesis and the absence of any risks with this operation, its use is suitable where primary or secondary intervertebral disc damage has occurred, in particular, at the onset of the illness before the occurrence of definitive damage to the bone and joints.

The nucleus prosthesis essentially consists of at least one movable body 8, made of a rigid, non-oxidizing, biocompatible material, capable of moving in two axes of a plane (for example, a stainless steel ball or a ball made of titanium), with a volume which is adapted to that of the biological nucleus. This movable body or ball 8 is mounted in a body 7 referred to hereinafter as cage, comprising a casing 14 (shown, by way of example, in FIG. 11) which is made of a light, rigid, non-oxidizing and biocompatible material (such as titanium), and this casing 14 contains a mass 15 made of a material having a minimum coefficient of friction (such as polyethylene). Inside there is a space for accommodating the movable body or ball 8, which is captured in this space, but is held so as to be freely rotatable about its center and in such a way that it emerges at each of the two opposite faces (upper and lower faces) of the cage 7 in the form of a spherical cap with a height which is approximately one tenth of the diameter of the movable body or ball 8, without this value having to be strictly adhered to.

The volume of the cage 7 accommodating the movable body 8 is itself adapted as closely as possible to the volume of the biological nucleus, but the fact that the cage 7 must serve as mounting for the ball 8 is, of course, taken into consideration. This allows the prosthesis to position itself so that it is always able to be in the anatomical position and thereby restore the natural movement between two vertebral bodies.

The cage 7 containing the ball 8 may have in a plan view (FIG. 8) a more or less curved shape, which is symmetrical in relation to a transverse center plane. In cross section (FIG. 10) the cage preferably has the shape of a trapezoid, the small end face of which contains the ends of the shape that is curved to a more or less pronounced extent.

Owing to this trapezoidal asymmetry of the cage 7, with front to back orientation, rotation thereof between the two vertebral bodies is prevented during displacement of thus constructed prosthesis accommodating the artificial nucleus (ball 8).

In a modified embodiment shown in FIGS. 12, 13 and 14, the cage 7, which in cross section has essentially the shape of an isosceles trapezoid (FIG. 13), can accommodate several identical balls 8 (FIG. 14) which at the outside touch a common imaginary plane on either side of the horizontal center plane of the cage. The balls are located on both faces of the cage 7 at the three corners of an isosceles triangle.

To enhance the comfort, the cage 7 according to the embodiments of FIGS. 15, 16 and 17 may consist of two single identical bodies 10, 11 which are rigid, unoxidizable and biocompatible and have the shape of an isosceles trapezoid. They are arranged such that their center planes extending at right angles to the parallel bases along their center lines are essentially parallel to each other and that the large bases of the single trapezoidal bodies 10 and 11 lie essentially in the same vertical plane.

The two single bodies formed in this way are connected to each other by two elastic bearing elements 12 and 13 which extend at right angles to the center planes of the single bodies 10 and 11 and are arranged close to the end of a large axis which itself forms a common tangent to the sets of balls 8 arranged on each outer face of the entire arrangement such that the balls are placed at the three corners of an isosceles triangle, which on opposite sides of the arrangement point in opposite direction.

When a prosthesis corresponding to FIGS. 8 to 17 is inserted, it will be understood that immediately after its introduction into the nucleus cavity, the prosthesis will assume the function of the biological nucleus and will place the intersecting fibers of the annulus under tension during movement sideways, forwards or backwards and thereby cause return to the balanced position. The quick operation necessary for its insertion eliminates any risk of traumatism and ensures rapid healing of the single necessary incision.

The final selection from the models proposed herein, all of which offer the same advantages in terms of insertion and physiological results, will be made in the course of time on the basis of the clinical results obtained.

Without departing from the concepts underlying the invention, the cage 7 containing a ball 8 or several balls 8, for which several embodiments have been proposed hereinabove, can, of course, also have other equivalent shapes. It is merely important that it serve as mounting for the ball or balls 8, that these be freely rotatable therein and that its volume be adapted to the volume available after removal of the biological nucleus.

With all of the above-described embodiments, the described nucleus prosthesis is able to take up its own position spontaneously in the anatomical surroundings, thus allowing all natural movements between two vertebral bodies to be restored (leaning sideways, leaning forwards and backwards, rotation). The conical shape (trapezoidal in cross section) of the cage 7 facilitates displacement in the plane of the end faces of the vertebrae and at the same time prevents rotation of the cage about its central axis as well as sinking of the implant into the end faces of the vertebrae.

The invention claimed is:

1. Intervertebral nucleus prosthesis comprising a cage and a substantially spherical body or ball, wherein:
   said prosthesis has dimensions adapted to a biological intervertebral nucleus,
   said cage has a shape elongated in one plane,
   said substantially spherical body or ball is made of a substantially rigid, substantially non-oxidizing, biocompatible material, is captured non-displaceably in said cage, is rotatable about at least two axes through its center within the cage, and protrudes at both opposite sides of said elongated plane of said cage in the form of substantially spherical caps.

2. Prosthesis in accordance with claim 1, wherein the cage is substantially planar, is curved in said plane and is substantially symmetrical in relation to a plane that is transverse to the plane of said cage and that includes a center axis in said cage.

3. Prosthesis in accordance with claim 2, wherein in cross section, the cage has the shape of an isosceles trapezoid comprising a narrow side and a wide side, with the ends of the curved shape arranged at the narrow side thereof, the trapezoidal shape facilitating displacement in the plane of the cage and preventing substantial rotation of the prosthesis about its center axis.

4. Prosthesis in accordance with claim 1, wherein the cage comprises a casing made of a light, substantially rigid, substantially non-oxidizing, biocompatible material, and contains a mass made of a material with a minimum coefficient of friction, and wherein a space for accommodating the movable substantially spherical body(s) is provided in the interior of the mass, said substantially spherical body(s) being held trapped but rotatable therein about at least two axes through its center.

5. Prosthesis in accordance with claim 4, wherein said casing comprises titanium.

6. Prosthesis in accordance with claim 5, wherein said mass comprises polyethylene.

7. Prosthesis in accordance with claim 4, wherein said mass comprises polyethylene.

8. Prosthesis in accordance with claim 1, wherein the cage has substantially the shape of an isosceles trapezoid and holds a plurality of substantially identical substantially spherical bodies which each touch, on both sides of the horizontal center plane of the cage, a substantially identical imaginary plane lying outside the cage, and which are located on both sides of the cage at the corners of an isosceles triangle.

9. Prosthesis in accordance with claim 8, wherein the substantially spherical bodies have a volume which, taking into consideration the function of the cage as holder for the substantially spherical bodies, is adapted as well as possible to the volume of the biological nucleus, thereby to ensure a self-positioning of the prosthesis, which allows the prosthesis to always be in the anatomical position and the natural movements between two vertebral bodies to be restored.

10. Prosthesis in accordance with claim 1, wherein the prosthesis comprises two cages each having a cross section in the shape of an isosceles trapezoid, which are arranged such that their center planes extending at right angles to the parallel bases and along their center lines are substantially parallel to each other, and wherein the large bases of the trapezoidal cages lie in a substantially vertical plane, said cages being connected to each other by at least two elastic connecting elements which extend at right angles to the center planes of said cases and are located in the end area of the large axis forming a common tangent to the sets of substantially spherical bodies which are each located on the outside of an arrangement of substantially spherical bodies at the corners of isosceles triangles, said triangles being oppositely orientated.

11. Prosthesis in accordance with claim 1, wherein the height of the substantially spherical cap protruding from the cage is approximately a tenth of the diameter of the substantially spherical body.

12. A prosthesis, adapted to replace a damaged nucleus of an intervertebral disc comprising an annulus, said prosthesis comprising:
   a cage of a substantially planar shape that is adapted to fit within said annulus and is thinner than a space that is adapted to be maintained between next adjacent vertebra that are adapted to be separated by said disc, and
   at least one substantially spherical body or ball disposed non-displaceably in said cage and rotatably about at least two axes through its center within the cage, and made of a substantially rigid, substantially non-oxidizing, biocompatible material, wherein said substantially spherical body(s) has a diameter that is greater than the planar thickness of said cage and is adapted to protrude from both opposite sides of said cage in the form of substantially spherical caps, wherein said spherical body or ball has a diameter such that it is adapted to be disposed in said space between said next adjacent vertebra and within the confines of said annulus.

13. A prosthesis as claimed in claim 12 wherein said substantially spherical body or ball is not substantially elastically deformable.

14. A method for implanting, within the confines of an annulus of an intervertebral disc, an intervertebral nucleus prosthesis comprising a substantially planar cage in which at least one substantially spherical body or ball is captured non-displaceably but rotatably about at least two axes through its center within the cage, said substantially spherical body or ball being made of a substantially rigid, substantially non-oxidizing, biocompatible material, with a diameter adapted to a biological nucleus and protruding at both opposite sides, in the form of substantially spherical caps from the cage, comprising the steps of:
   for insertion of the prosthesis consisting of the cage and substantially spherical bodies, making an incision endoscopically in an annulus that is disposed between two vertebral bodies, thereby providing an opening which is just large enough to reach and remove a damaged nucleus;
   removing said damaged nucleus through said incision;
   substantially immediately after removal of said damaged nucleus, inserting, through the same incision, said nucleus prosthesis which automatically centers itself in the cavity formed by the removal of said damaged nucleus, and
   subsequently closing said incision.

15. The method of claim 14, wherein said incision is closed by a suture.

\* \* \* \* \*